(12) United States Patent
Falk et al.

(10) Patent No.: US 11,207,020 B2
(45) Date of Patent: Dec. 28, 2021

(54) FETAL MONITORING HUB

(71) Applicant: General Electric Company, Schenectady, NY (US)

(72) Inventors: Steven Mitchell Falk, Laurel, MD (US); Serguei Kabakov, Laurel, MD (US); Daniel Williams Medeiros, Laurel, MD (US); Aimee Klussendorf, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 466 days.

(21) Appl. No.: 15/193,466

(22) Filed: Jun. 27, 2016

(65) Prior Publication Data

US 2017/0367643 A1 Dec. 28, 2017

(51) Int. Cl.
*A61B 5/00* (2006.01)
*A61B 5/024* (2006.01)
(Continued)

(52) U.S. Cl.
CPC .......... *A61B 5/4362* (2013.01); *A61B 5/002* (2013.01); *A61B 5/0011* (2013.01); *A61B 5/0022* (2013.01); *A61B 5/02411* (2013.01); *A61B 5/035* (2013.01); *A61B 5/14542* (2013.01); *A61B 5/288* (2021.01); *A61B 5/318* (2021.01); *A61B 5/4356* (2013.01);
(Continued)

(58) Field of Classification Search
CPC . A61B 5/4362; A61B 5/4356; A61B 5/02411; A61B 8/0866; A61B 5/02438; G06F 12/0815–0837; G06F 1/3212; G06F 1/3287; G16H 40/67; G16H 40/60; G16H 40/63; H04L 67/12; H04L 67/125
See application file for complete search history.

(56) References Cited

U.S. PATENT DOCUMENTS

| 6,816,744 B2* | 11/2004 | Garfield | ............... A61B 5/4362 |
| | | | 600/511 |
| 7,020,508 B2* | 3/2006 | Stivoric | ............. A61B 5/02438 |

(Continued)

OTHER PUBLICATIONS

Kanjilal, et al. "Fetal ECG extraction from single-channel maternal ECG using singular value decomposition." IEEE Transactions on Biomedical Engineering 44.1 (1997): 51-59.*

(Continued)

*Primary Examiner* — David J. McCrosky

(57) ABSTRACT

In the present invention, a system and associated method is provided for monitoring fetal vital parameters. The system includes a base unit, a monitoring hub including a digital signal processor/controller and operably connected to the base unit by a single channel digital signal protocol cable, e.g., a USB cable, and a number of fetal monitoring sensors operably connected to the monitoring hub. The controller processes the signals from the sensors into a single USB protocol which can be sent along a single cable to the base unit. The USB cable allows power to be supplied to the hub in order to charge a battery used to operate the hub and the sensors connected to the hub when disconnected from the base unit to allow the patient using the hub to move freely about the base unit, with all sensor signals from the hub being wirelessly transmitted to the base unit.

18 Claims, 3 Drawing Sheets

(51) Int. Cl.
*G06F 1/3287* (2019.01)
*A61B 8/08* (2006.01)
*A61B 5/145* (2006.01)
*H04L 29/08* (2006.01)
*A61B 5/318* (2021.01)
*A61B 5/03* (2006.01)
*A61B 5/288* (2021.01)
*G06F 1/3212* (2019.01)
*G16H 40/67* (2018.01)

(52) U.S. Cl.
CPC .............. *A61B 5/6823* (2013.01); *A61B 5/72* (2013.01); *A61B 8/488* (2013.01); *G06F 1/3212* (2013.01); *G06F 1/3287* (2013.01); *H04L 67/12* (2013.01); *A61B 2560/0209* (2013.01); *A61B 2560/0214* (2013.01); *G16H 40/67* (2018.01)

(56) References Cited

U.S. PATENT DOCUMENTS

| | | | |
|---|---|---|---|
| 7,758,522 B2 | 7/2010 | Pandit | |
| 8,170,656 B2* | 5/2012 | Tan | G06F 1/163 600/546 |
| 8,868,164 B2* | 10/2014 | Kabakov | A61B 5/4362 600/511 |
| 9,116,695 B2* | 8/2015 | Yasui | G06F 1/3287 |
| 9,168,022 B2 | 10/2015 | Kabakov et al. | |
| 2008/0309774 A1* | 12/2008 | Beng Goh | H04N 13/10 348/218.1 |
| 2009/0112630 A1* | 4/2009 | Collins, Jr. | G16H 40/67 705/3 |
| 2012/0089369 A1* | 4/2012 | Abuzeni | G16H 40/67 702/188 |
| 2014/0249383 A1* | 9/2014 | Jeanne | A61B 5/4356 600/301 |
| 2014/0249436 A1* | 9/2014 | Kabakov | A61B 5/6806 600/509 |
| 2014/0313052 A1* | 10/2014 | Yarger | A61B 5/14532 340/870.02 |
| 2015/0272466 A1* | 10/2015 | Laakkonen | A61B 5/0416 600/522 |
| 2017/0134536 A1* | 5/2017 | Tessiore | H04L 69/18 |

OTHER PUBLICATIONS

Internet Archive, Wallace Surgical website "Fetal2EMR Fetal Monitor" May 6, 2015. Retrieved from <https://web.archive.org/web/20150506164547/http://www.wallachsurgical.com/products/obstetrics/fetal-monitors/fetal2emr/> on Jul. 24, 2018.*

Capano, Daniel E. "Choosing between single and multi-channel architecture" Sep. 10, 2015. Retrieved from <https://www.controleng.com/single-article/choosing-between-single-and-multi-channel-architecture/87fb639c07aac0135c8217a02ac5eeb3.html> on Jul. 24, 2018.*

Internet Archive, Hu et al "Ways to Use USB in Embedded Systems" smxrtos.com. Jun. 23, 2015. <https://web.archive.org/web/20150623151411/http://www.smxrtos.com/articles/usb_art/waysusb.htm> (Year: 2015).*

* cited by examiner

FETAL MONITORING HUB

BACKGROUND OF INVENTION

The subject matter disclosed herein relates to the field of fetal monitoring devices and methods, and more specifically to fetal monitoring devices connected to separate displays.

To continually monitor the vital statistics of a fetus prior to delivery, or in any other situation where the fetus would require continual monitoring, a fetal monitor is positioned on the mother at a location where the monitor can detect the vital statistics/signs of the fetus being carried by the mother. This monitor is also connected to a suitable display in order for the signals/vital parameters from the fetus that are detected by the fetal monitor to be displayed for review by a physician.

The fetal monitors currently in use employ a number of sensors/transducers that are connected to the monitor and detect and transmit information to the display regarding different vital signs/parameters for the fetus.

One significant drawback to prior art fetal monitoring devices is that the fetal monitor requires a separate lead for each of the sensors from the sensor to the monitor in order to enable the monitor to receive the signal from the sensor. The leads for each sensor are connected to different ports on the monitor in order to separate the various signals from one another for proper conditioning and display the signals by the monitor. As a result, there is the potential for the misconnection of one or more of the leads to the monitor, which would provide incorrect data to the physician on the condition/vital parameters of the fetus.

In addition, in order to maintain the fetal monitor operational, in many prior art monitors the sensors must remain connected to the monitor. This connection ensures that the fetal sensors remain powered by the monitor to provide the signals to the monitor for effective observation and monitoring of the fetus. Thus, the mobility of the mother is limited as the sensors must remain connected to the monitor, requiring the mother to remain within the length of the leads from the sensors to the monitor or to move the monitor in conjunction with the mother. And, even when a mother may need to disconnect from the monitor in order to move to the restroom, or a different location, such as a chair, in her room, such disconnection requires the unplugging of multiple cable leads and the management of the multitude of cable leads. Currently, the cable leads are managed by slinging the cable leads around the mother's neck, and it's common to find the cable leads tangled and/or twisted in such a way that makes reconnection to the monitor challenging.

To attempt to address this limitation, in other prior art monitors the sensors can be wirelessly connected to the monitor to transmit the signals obtained by the sensors. However, with these monitors the sensors must be individually powered, normally requiring a battery that is disposed within the body of the sensor. As such, the sensors have to be individually recharged in some manner, e.g., by replacing or recharging the batteries, to maintain the sensors operational, which can be time intensive. Further, as the sensors are wirelessly connected to the monitor, the signals transmitted from the sensors to the monitor can encounter interference or other issues that degrade the signals prior to reaching the monitor, which consequently lessens the effectiveness of the signals for fetal monitoring purposes.

Additionally, as prior art fetal monitors require separate signals from the individual sensors to be received by the monitor either via a lead or wirelessly, the signals from each sensor can have different protocols. This requires that the monitor be programmed to receive the protocols for the individual signals, increasing the complexity of the programming for the monitor and consequent updates to the programming.

Hence it is desirable to provide an improved fetal monitor that addresses these shortcomings.

BRIEF DESCRIPTION OF THE INVENTION

There is a need or desire for a fetal monitor and method of operation that does not include the above-mentioned drawbacks and needs in the prior art. These issues are addressed by the embodiments described herein in the following description of the invention, which is a system and method for increasing the angular positions for the detector in which the procedure can be performed and without the need for the clinician/physician performing the procedure to place their hands within the beam striking the detector.

In the exemplary embodiments of the monitor and associated method, a fetal monitor includes a hub that is connected between the sensors positioned on the mother to monitor the fetus and the monitor. The hub is a single channel, e.g., USB, type hub that manages the data flow and sensor configurations, as well as directing the data flow to the monitor. The hub is connected to the monitor by a USB cable that enables the hub to transfer signals from the sensors to the monitor. The USB cable also enables the monitor to supply power to the hub. In turn, the hub can power the sensors connected to the hub.

According to other exemplary embodiments of the invention, the hub includes a wireless module and a rechargeable battery to allow unplugging the USB to the monitor. The rechargeable power source is charged by the USB cable connected between the monitor and the hub. When the cable is disconnected from the hub, the power source within the hub powers the hub and the sensors connected to the hub. In addition, the signals received from the sensors are transmitted wirelessly from the hub to the monitor by the module, enabling the hub to be moved freely around the monitor without the physical cable connection between the hub and the monitor.

According to one exemplary embodiment of the invention, a fetal monitoring system includes a base unit, a monitoring hub including a digital signal processor/controller a wireless transceiver module capable of receiving and transmitting single channel wireless signals to and from the base unit and a single cable input/output port adapted to receive a single channel digital signal protocol cable therein, and at least one fetal monitoring sensor operably connected to the monitoring hub.

According to another exemplary embodiment of the invention, a monitoring hub for a fetal monitoring system includes a digital signal processor/controller adapted to receive signals from a number of fetal monitoring sensors and then transmit signals in a single digital protocol to a monitor, a wireless transceiver module operably connected to the digital signal processor/controller and the power source, a single cable input/output port adapted to receive a single channel digital signal protocol cable therein and a power source operably connected to the digital signal processor/controller.

According to still another exemplary embodiment of the invention, a method of monitoring the fetal vital parameters of a patient includes the steps of providing a fetal monitoring system including a base unit, a monitoring hub including a digital signal processor/controller, a wireless transceiver module capable of receiving and transmitting single channel, wireless signals to and from the base unit and a single cable input/output port adapted to receive a single channel digital signal protocol cable therein, and at least one fetal monitoring sensor operably connected to the monitoring hub, placing the at least one sensor on a patient to sense a fetal parameter and generate signal in response thereto, transmitting the signal to the monitoring hub, configuring the signal in the monitoring hub from the at least one sensor into a single channel digital protocol and transmitting the single channel digital protocol signal from the monitoring hub to the base unit.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure

BRIEF DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Exemplary embodiments of the invention disclosed herein relate to a system and method for monitoring the vital signs of a fetus using sensors disposed on the patient including a hub connected between the sensors and the monitor.

Figure 1:
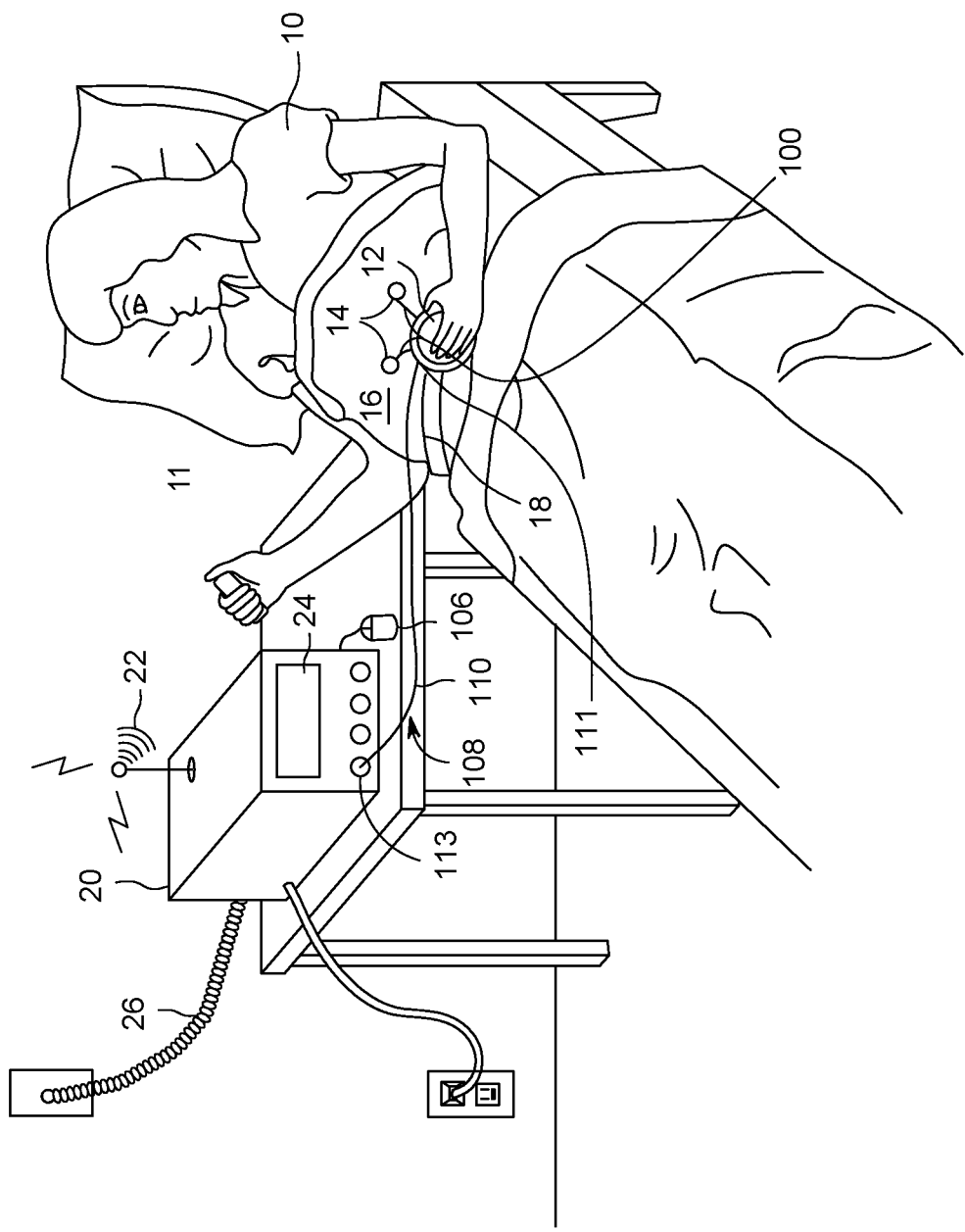
FIG. 1 is a schematic view a patient utilizing a fetal monitoring system according to an exemplary embodiment of the invention.

An example of a fetal monitoring system 12 designed to acquire signals regarding the vital parameters or signs of a fetus utilizing non-invasive or invasive transducers, such as the fetal heart rate (FHR) and uterine activity (UA) is provided in FIG. 1. In the embodiment illustrated in FIG. 1, the monitoring system 11, such as that disclosed in U.S. Pat. No. 7,758,522 entitled Combined Uterine Activity and Fetal Heart Rate Monitoring Device, which is hereby expressly incorporated by reference in its entirety for all purposes, depicts a pregnant patient 10 who is having the fetal heart rate (FHR) and uterine activity (UA) non-invasively monitored by the monitoring system 11. The monitoring system 11 comprises a plurality of sensors 14 that are attached to the abdomen 16 of the patient 10 for measuring certain parameters of the fetus. The plurality of sensors 14 can include multiple different sensors 14 for measurement of different vital parameters, and can include multiple sensors 14 of the same type, such as to monitor the same vital parameters for more than one fetus present within the patient 10. The sensors 14 may comprise one or more Doppler ultrasound/ultrasonic transducers for the measurement of the fetal heart rate and one or more tocodynamometers/electrodes for measuring uterine contractions/activity. Additionally, the monitoring system 11 can optionally utilize invasive sensors (not shown) such as fetal scalp electrodes or intra-uterine pressure catheters, among other fetal intrauterine sensors, as well as sensors attached and used to monitor the vital parameters of the patient 10, such as maternal electrocardiogram and/or pulse oximeter sensors to measure the maternal heart rate and maternal tissue oxygen concentration, among other optional maternal sensors.

In one exemplary embodiment, the sensors 14 are each connected to a monitoring hub 12. The data obtained by the sensors 14 is digitally transmitted along leads 100 that extend between the hub 12 and the sensors 14. The leads 100 are connected to the hub 12 at a number of sensor input ports 102 (FIG. 2) that can be configured to match the particular sensor 14 to be connected to the particular port 102, or can be universal ports 102 allowing a lead 100 from any sensor 14 to be connected to any port 102.

The hub 12 is designed to worn on the body of the patient 10, such that the hub 12 can move with the patient 10. In the illustrated exemplary embodiment, the hub 12 is held in place on the abdomen 16 of the patient 10 by an elastomeric band 18. The elastomeric band 18 is attached to the monitoring hub 12 and extends around the abdomen of the patient 10, thereby holding the monitoring hub 12 in a secure position. Alternatively, the hub 12 can be formed with a suitable clip (not shown) that is engagable with the hub 12 in order to enable the clip to hold the hub 12 on the patient 10 in an easily removable manner, such as by engaging the clip with a belt (not shown) or pocket on a garment being worn by the patient 10. Further, while the size of the hub 12 can be selected as desired, in one exemplary embodiment the hub 12 has a size similar to a cellular phone to render the hub 12 easily portable by the patient 10.

A monitor/base unit 20 associated with the patient 10 can receive, process, display, and/or store patient physiological data that is collected by the monitoring hub 12 and transmitted to the base unit 20. The base unit 20 may further comprise a display 24 for displaying the physiological parameters monitored by the monitoring hub 12 attached to the sensors 14 secured to the patient 10. The display 24 may display a digital signal that is received from the sensors 14 via that hub 12 indicative of the sensed parameters of the patient 10, such as the fetal heart rate, an uterine activity among others. The base unit 20 may also include a suitable user input device 106, such as a mouse and/or keyboard, to enable an individual to interact with the information being relayed to and displayed on the base unit 20.

The base unit 20 may further be connected to a hospital network (not depicted) via a network data connection 26. The network data connection 26 may be a wired or wireless network connection that transmits data to and from the base unit 20 and a hospital data network or server. In an embodiment utilizing a hospital server or network, the base unit 20 may store physiological data collected from the patient 10 such that the physiological data may be accessed at a later time.

Figure 2:
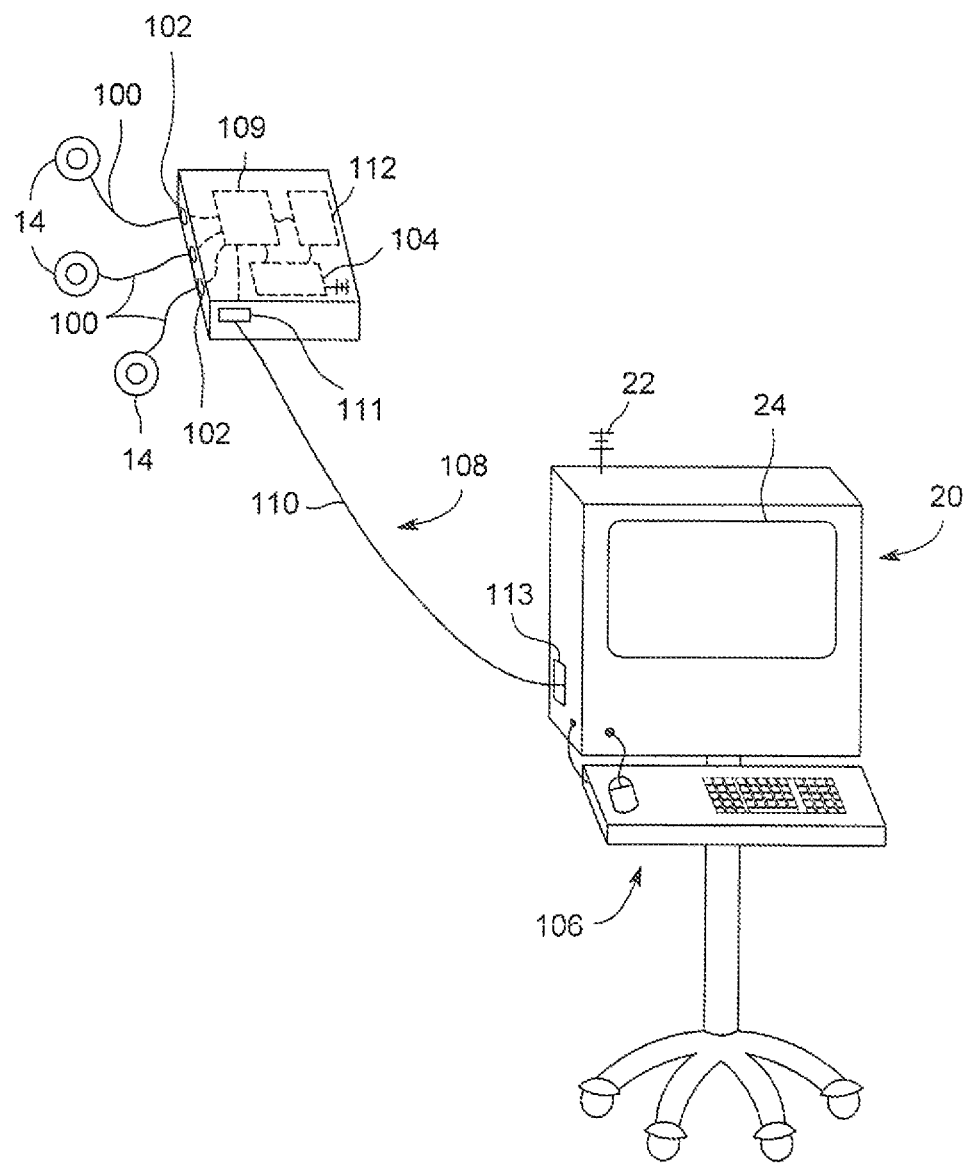
FIG. 2 is a schematic diagram of an embodiment of a system for monitoring a pregnancy according to another exemplary embodiment of the invention.

Looking now at FIGS. 1 and 2, in order to transmit the digital data from the sensors 14 to the base unit 20, the base unit 20 may comprise an antenna 22 to receive wireless communications in any suitable wireless protocol, such as Bluetooth®, WiFi, etc. from a wireless transceiver module 104 disposed on or associated with the hub 12. Alternatively, the monitoring hub 12 may send digital data to the base unit 20 via a data cable 108 extending between the hub 12 and the base unit 20. In the exemplary illustrated embodiment, the monitoring hub 12 is a single channel digital signal protocol hub, such as a universal serial bus (USB) protocol type hub with a suitable USB controller/digital signal processor 109 disposed therein that performs a variety of operational and control functions, such as those disclosed in U.S. Pat. No. 9,168,022, entitled Abdominal Sonar System and Apparatus, which is expressly incorporated herein in its entirety by reference for all purposes. The controller 109 can operate and manage the various functions of the hub 12 including managing the digital data flow from the sensors 14 through the hub 12 to the base unit 20 for display and managing the configurations for the sensors 14 as determined using the user input 106 on the base unit 20. Being a USB protocol hub 12, the controller 109 disposed within the hub 12 can configure the digital data received from each of the respective sensors 14 to transmit the data from a cable input/output port 111 on the hub 12 along a single USB cable 110 to a suitable cable port 113 on the base unit 20 in a format that allows the signals from each of the sensors 104 to be sent along the cable 100 via a single channel (USB protocol) that can be readily utilized by the base unit 20. Further, with the standardization of the sensor signals supplied to the base unit 20 from the USB controller 109 within the hub 12, the hub 12 and/or base unit 20 can be readily upgradable, without having to provide multiple upgrades corresponding to the signal formats for the individual sensor signals, to facilitate the communications and digital data transfer between the sensors 14 and the base unit 12.

In addition, because as power can be transmitted along the USB cable 110 from the base unit 20 to the hub 12, the hub 12 can be directly powered by the base unit 20 when connected to the base unit 20 using the cable 110. Thus, by employing a single USB cable 110 between the monitoring hub 12 and the base unit 20, the set up and operation of the system 11 is significantly streamlined by minimizing the number of cables 108 to be connected between the hub 12 and base unit 20, virtually eliminating the potential for misconnection of cables and the corresponding issues with incorrect information displays on the base unit 20.

In another exemplary embodiment of the invention, the monitoring hub 12 includes a rechargeable battery 112 that is operably connected to the controller 109. When connected to the base unit 20 using the USB cable 110, the battery 112 is charged by the power supplied from the base unit 20 through the USB cable 110. Thus, when the cable 100 is unplugged from the hub 12 and/or the base unit 20, such as to allow the patient 10 to move around, the hub 12 is supplied with power via the battery 112. In this manner digital signals from the sensors 14 connected to the hub 12 can be routed wirelessly from wireless module 104 on the hub 12 directly to the base unit 20. Further, in the exemplary embodiment where the sensors 14 are connected via leads 100 to the hub 12, the power supply/battery 112 within the hub 12 can be used to power the sensors 14.

In still other exemplary embodiments, the sensors 14 can be wirelessly connected to the hub 12 to send signals to the wireless module 104 for transmission from the hub 12 to the base unit 20, either wirelessly or through the cable 110. Also, in other situations the controller 109 can selectively operate the hub 12 based on the operational parameters of the hub 12 determined by the controller 109, including the charge level of the battery 112 and the data stream incoming to the hub from the sensors 14, among others, to optimize the connection between the hub 12 and the base unit 20. For example, when the charge on the battery 112 is low, the controller 109 can operate the hub 12 to enable the battery 112 to be charged through the cable 110 while data is wirelessly transmitted between the hub 12 and the base unit 20. Further, in situations where the battery 112 is fully charged, all data transmission can occur through the cable 110, without any corresponding power transmission.

Figure 3:
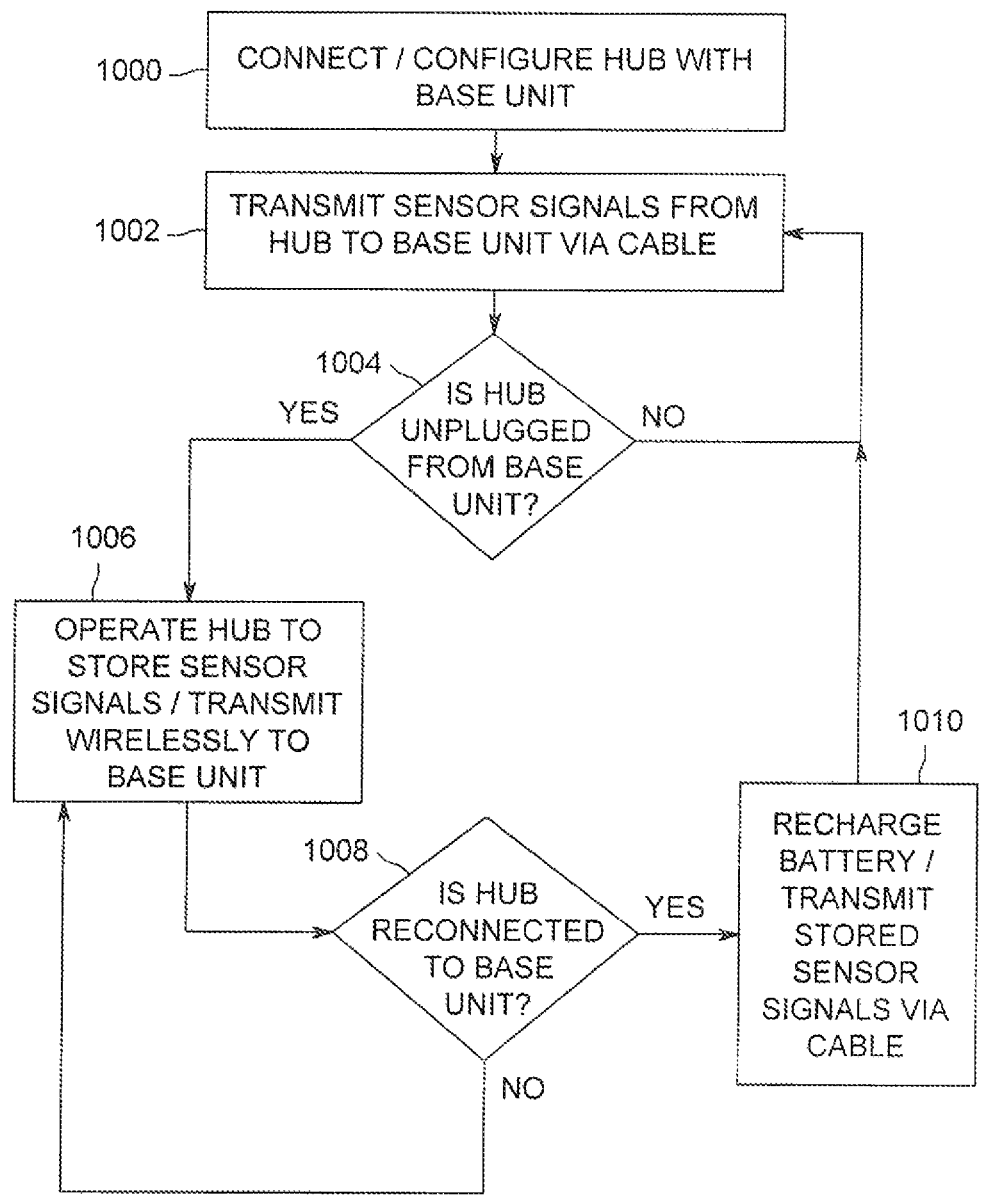
FIG. 3 is a schematic view of a method of monitoring a pregnancy using a fetal monitoring system according to an exemplary embodiment of the invention.

The hub 12 provides lead cable management for the pregnant patient 10 and clinicians with respect to the monitor/base unit 20 in that, in one embodiment, a single data cable 108 may extend between the hub 12 and the base unit 20. In use, such as in the exemplary method of monitoring the patient 10 using the hub 12 shown in FIG. 3, initially in block 1000 the hub 12 is operatively connected to and configured to communicate with the base unit 20 in a known manner, such as by connecting the cable 108 to the input/output port 11 or by wirelessly connecting the hub 12 to the base unit 20. Once configured, the hub 12 can transmit signals, from the sensors 14 through the hub 12 to the base unit 20 in block 1002 for the monitoring of the patient 10.

To allow for mobility of the pregnant patient 10, the data cable 108 may be unplugged from the cable input/output port 111 on the hub 12. The patient may then move about untethered to the base unit 20. In the untethered state, which is sensed by the hub 12 in decision block 1004, the hub 12 may be configured to store a cache of data that will be transmitted once reconnected to the base unit 20 in block 1006. In another embodiment, in block 1006 the hub 12 may wirelessly transmit data via the wireless module 104 in real time to base unit 20. It should be appreciated, however, that when the pregnant patient 10 is in the untethered state there it is envisioned that there are no loose or unconnected sensor leads 100 which can get tangled or twisted. Additionally, no sensor leads 100 need to be slung around the patient's neck.

When the pregnant patient 10 returns to a location proximate the based unit 20, such that the cable 108 is able to span the distance between the hub 12 and the base unit 20, only a single cable, the data cable 108 is needed to be reconnected to the hub at port 111 to restore the transmission of data via the cable 108. In one embodiment, when the hub 12 is reconnected to the base unit 20 via the data cable 108 as sensed or determined by the hub 12 in decision block 1008, the cache of data collected by the hub in the untethered state may be transmitted and the power source/battery 112 recharged via the cable in block 1010. Further, as long as the hub 12 remains connected to the base unit by the cable 108, the hub 12 can continue to transmit the signals/data from the sensors 14 to the base unit 20 via the cable 108, in block 1002.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fetal monitoring system comprising:
a base unit;
a monitoring hub including a digital signal processor/controller, a wireless transceiver module capable of receiving and transmitting single channel wireless signals from and to, respectively, the base unit and a single cable input/output port adapted to receive a single channel digital signal protocol cable therein; and
multiple monitoring sensors operably connected to the monitoring hub, wherein the controller is configured to standardize sensor signals from each of the multiple sensors for transmission along a single channel and transmit sensor data from each of the multiple sensors via the single channel,
wherein the monitoring hub is configured to cache data from the sensors when disconnected from the base unit,
wherein the base unit is configured to supply power to the monitoring hub along a USB cable and the monitoring hub is configured to provide the sensor data wirelessly to the base unit in response to detecting a charge of a battery of the monitoring hub is below a threshold, and the monitoring hub is configured to provide the sensor data to the base unit using the USB cable in response to detecting the battery is charged, and
wherein the multiple sensors are selected from the group consisting of one or more non-invasive fetal monitoring sensors, one or more invasive fetal monitoring sensors, and combinations thereof.

2. The system of claim 1 further comprising a single channel digital signal protocol cable inserted within the single input/output port.

3. The system of claim 2 wherein the single channel digital signal protocol cable is a USB cable.

4. The system of claim 1 wherein the multiple sensors are each operably connected to the monitoring hub via a lead.

5. The system of claim 1 wherein the monitoring hub includes a power source.

6. The system of claim 5 wherein the power source is rechargeable.

7. The system of claim 6 wherein the power source is rechargeable via the cable.

8. The system of claim 5 wherein the power source supplies power to the multiple sensors.

9. A hub for a fetal monitoring system, the hub comprising:
a digital signal processor/controller adapted to receive signals from a number of fetal monitoring sensors and transmit the signals in a single digital protocol to a monitor and to control the hub based on operational configurations that include an incoming data stream from fetal monitoring sensors, wherein each of the signals comprises sensor data from one of the fetal monitoring sensors;
a power source operably connected to the digital signal processor/controller;
a wireless transceiver module operably connected to the digital signal processor/controller and the power source; and
a single cable input/output port adapted to receive a single channel digital signal protocol cable therein,
wherein the hub is configured to cache data from the sensors when disconnected from a fetal monitoring system base unit,
wherein the fetal monitoring system base unit is configured to supply power to the hub along a USB cable and the hub is configured to provide the sensor data wirelessly to the fetal monitoring system base unit in response to detecting a charge of a battery of the hub is below a threshold, and the hub is configured to provide the sensor data to the fetal monitoring system base unit using the USB cable in response to detecting the battery is charged, and
wherein the number of sensors are selected from the group consisting of: at least two or more of a Doppler ultrasound/ultrasonic transducer, a tocodynamometer, a fetal scalp electrode, an intra-uterine pressure catheters, a maternal electrocardiogram, a pulse oximeter sensor, and combinations thereof.

10. The hub of claim 9 further comprising a number of sensor input ports.

11. The hub of claim 9 wherein the power source is adapted to be connected to the number of fetal monitoring sensors.

12. The hub of claim 9 wherein the single digital protocol is a USB protocol.

13. A method of monitoring fetal vital parameters of a patient, the method comprising:
providing a fetal monitoring system including a base unit, a monitoring hub including a digital signal processor/controller, a wireless transceiver module capable of receiving and transmitting single channel wireless signals to and from the base unit and a single cable input/output port adapted to receive a single channel digital signal protocol cable therein, and a number of fetal monitoring sensors operably connected to the monitoring hub,
wherein the processor/controller is configured to cache data from the number of fetal monitoring sensors when disconnected from the base unit;
placing the at least one sensor on a patient to sense a fetal parameter and generate signal in response thereto;
transmitting the signal to the monitoring hub;
configuring the signal in the monitoring hub from each of the number of fetal monitoring sensors into a single channel digital protocol; and
transmitting the single channel digital protocol signal from the monitoring hub to the base unit, wherein the single channel digital protocol signal comprises sensor data from each of the fetal monitoring sensors,
wherein the base unit is configured to supply power to the monitoring hub along a USB cable and the monitoring hub is configured to provide the signal wirelessly to the base unit in response to detecting a charge of a rechargeable battery of the monitoring hub is below a threshold, and the monitoring hub is configured to provide the signal to the base unit using the USB cable in response to detecting the rechargeable battery is charged, and
wherein the fetal monitoring sensors are selected from the group consisting of one or more non-invasive fetal monitoring sensors, one or more invasive fetal monitoring sensors, and combinations thereof.

14. The method of claim 13 wherein configuring the signal comprises configuring the signal into a USB protocol.

15. The method of claim 14 wherein transmitting the single channel signal comprises:
connecting the monitoring hub to the base unit by inserting a USB cable into the single input/output port; and
sending the signal along the USB cable.

16. The method of claim 14 wherein transmitting the signal to the base unit comprises wirelessly transmitting the signal.

17. The method of claim 13 wherein supplying power to the monitoring hub comprises charging the rechargeable battery within the monitoring hub.

18. The method of claim 13 further comprising supplying power to the number of monitoring sensors through the monitoring hub simultaneously with supplying power to the monitoring hub.

* * * * *